United States Patent
Buijsse et al.

(10) Patent No.: US 7,317,515 B2
(45) Date of Patent: Jan. 8, 2008

(54) METHOD OF LOCALIZING FLUORESCENT MARKERS

(76) Inventors: Bart Buijsse, P.O. Box 80066, Eindhoven (NL) 5600 KA; Robert Frans Maria Hendriks, Overlangelseweg 4, Overlangel (NL) 5371 PN ( * ) Notice: Subject to any disclaimer, the term of this patent is extended or adjusted under 35 U.S.C. 154(b) by 178 days.

(21) Appl. No.: 11/268,975

(22) Filed: Nov. 8, 2005

(65) Prior Publication Data

US 2006/0098188 A1    May 11, 2006

(30) Foreign Application Priority Data

Nov. 9, 2004  (NL) .................................... 1027462

(51) Int. Cl.
 *G01N 21/64*  (2006.01)
 *G01N 23/225* (2006.01)

(52) U.S. Cl. .................. 356/72; 356/318; 356/417; 356/615; 356/620

(58) Field of Classification Search ............. 356/72, 356/615, 620
See application file for complete search history.

(56) References Cited

U.S. PATENT DOCUMENTS 5,479,024 A    12/1995  Hillner et al.
5,811,804 A    9/1998   Van Blitterswijk et al.
6,002,471 A    12/1999  Quake
6,259,104 B1   7/2001   Baer

FOREIGN PATENT DOCUMENTS

DE    4233686 A1    4/1994
FR    2596863 A     7/2001

OTHER PUBLICATIONS

R. V. Krishman, R. Varma, and S. Mayor, "Fluorescence Methods to Probe Nanometer-Scale Organization of Molecules in Living Cell Membranes," Journal of Fluorescence vol. 11, No. 3, Sep. 2001 pp. 211-226.

*Primary Examiner*—F. L. Evans

(57) ABSTRACT

The invention describes a method of determining the position of fluorescent markers in a sample (4), with a high spatial resolution. To this end, the sample (4) is illuminated with an exciting light beam (11), while the sample (4) is simultaneously scanned by a particle beam (3). During scanning, markers will be impinged upon by the particle beam (3) and will be damaged, in such a manner that the marker impinged upon will no longer emit fluorescence radiation. This leads to a reduction of the flux of fluorescence radiation. This reduction is detected. Seeing as the position of the particle beam (3) w.r.t. the sample is known at the moment that the marker is damaged, the position of the marker in the sample is, accordingly, also known.

20 Claims, 2 Drawing Sheets

METHOD OF LOCALIZING FLUORESCENT MARKERS

Figure 1:
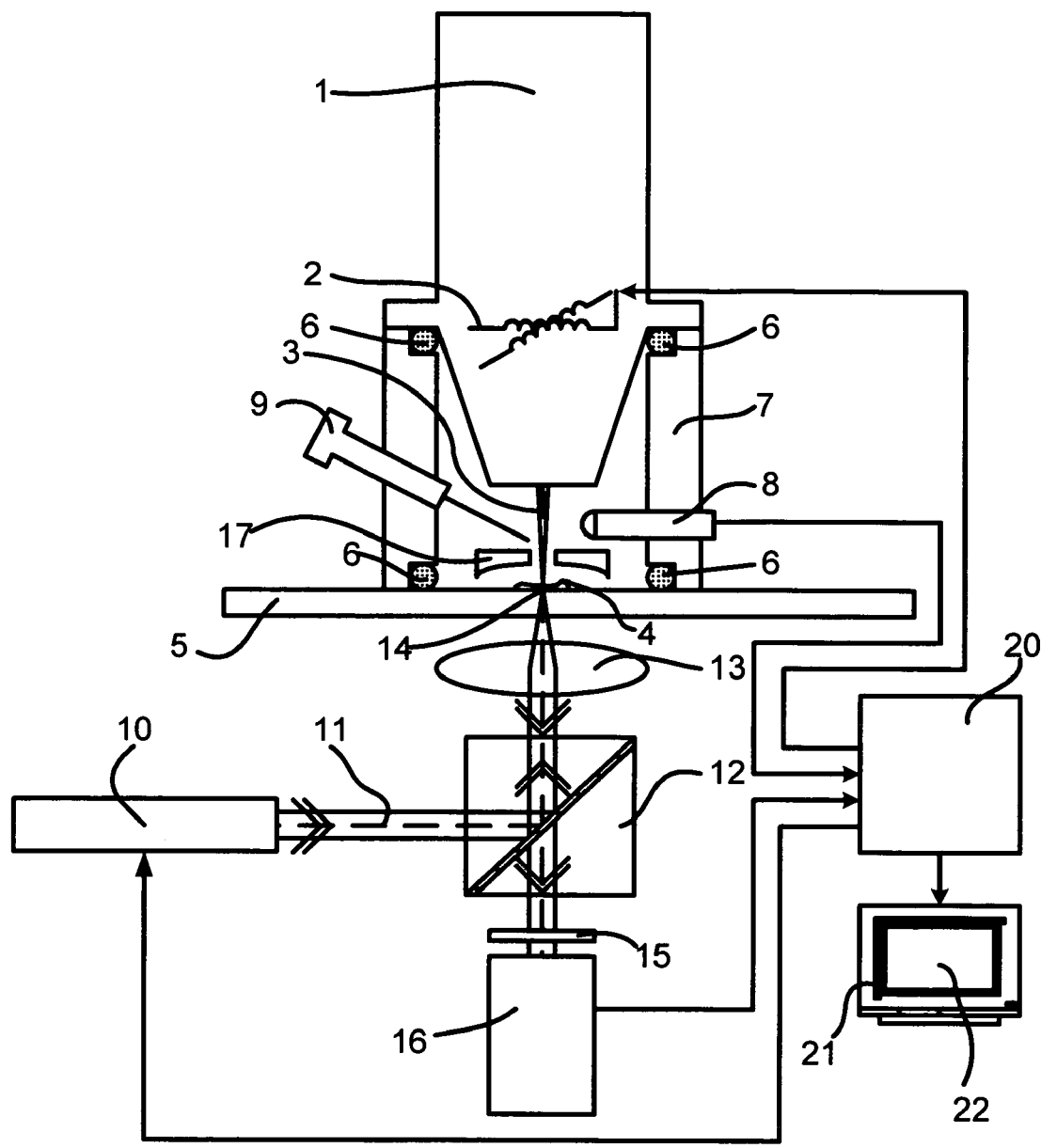

The invention relates to a method of localizing markers that are excitable by radiation in a sample to be investigated, comprising:

Providing markers in the sample;

Irradiating the sample with a first radiation beam, as a result of which an excitation region is formed in the sample, in which excitation region markers are excited;

Detecting fluorescence radiation emanating from markers in response to the excitation, and;

Preventing, with the aid of a second radiation beam, the detection of fluorescence radiation in a portion of the excitation region.

The invention also relates to an apparatus embodied to perform the method.

Such a method is known from text U.S. Pat. No. 6,259,104.

In biology and histology there is a need to determine the location of certain molecules, such as proteins, antibodies and nucleotides, in, for example, biological samples, so as to gain insight as to where and how certain processes occur in, for example, biological samples.

Fluorescence microscopy (FM) is a generally employed method in biology and histology that makes this possible. To this end, so-called fluorescent markers (hereafter referred to simply as "markers") are attached to the important molecules. These markers are characterized in that they attach themselves very specifically to, for example, certain types of antibodies, without attaching themselves to other types of antibodies and other molecules. Furthermore, these markers are characterized in that, in response to excitation by, for example, photons, they emit fluorescence radiation.

In this manner, the possibility arises of determining the position of, for example, a certain type of antibody in a sample, by attaching markers to this type of antibody and, subsequently, determining the position of the marker by means of the fluorescence radiation emitted by the marker.

It should be noted that the markers used for FM can be classified into organic markers and inorganic markers.

Organic markers generally comprise aromatic rings. Examples are FITC (fluorescein isothiocyanate), TRITC (tetramethylrhodamine isothiocyanate) and DAPI (bisbenzimide). Many types of organic markers are commercially available, each with its own attachment properties. Such organic markers are sold nowadays by, for example, the firm Molecular Probes, Inc., Eugene, Oreg., USA.

A typical property of these organic markers is that they have a limited lifetime: under the influence of photochemical reactions, the lifetime of such a marker will be limited to, for example, $10^5$ emitted photons. This has consequences for the time during which a marker can be excited. This will be returned to later. Moreover, the fluorescent action in these markers is influenced by environmental influences, such as, for example, the acidity (pH), temperature, the presence of solvents, etc., in the sample in which they are located.

Inorganic markers contain a nanocrystal of an inorganic material, such as CdSe, with a diameter of a few nanometers to a few tens of nanometers, which nanocrystal demonstrates fluorescence. This nanocrystal is bonded to organic reactive groups, which attach the marker to the molecule to be marked, such as a protein, and which determine the specific attachment behavior of the marker. Such inorganic markers are sold nowadays by, for example, the firm Biocrystal Ltd., Westerville, Ohio, USA.

Inorganic markers are characterized by a much greater lifetime and a lower sensitivity to environmental influences than the organic markers.

In the case of conventional FM, a sample in which fluorescent markers are present is illuminated using a light beam, such as a focused laser beam. Markers in the illuminated region, the so-called excitation region, are consequently excited and, in response to this excitation, emit a flux of fluorescence radiation. By detecting whether fluorescence radiation is emitted in response to the excitation, one can determine whether markers are located in the excitation region. The spatial resolution in this method is determined by the size of the focus of the light beam. In general, this focus cannot be smaller than the wavelength of the employed light. The employed wavelength cannot be chosen freely, seeing as only light within a given bandwidth of the wavelength will excite a certain type of marker. As a result, the spatial resolution of conventional FM is limited to approx. 500 nm.

Amongst users of FM, there is a desire to continue to reduce the spatial resolution of FM, preferably to molecular scales, i.e. a few nanometers.

In the cited patent text, a method is described whereby the resolution is improved with respect to conventional FM.

The sample is hereby briefly illuminated using a first radiation beam, which forms an excitation region in the sample, after which a second radiation beam prevents the detection of fluorescence radiation. The first radiation beam is a laser beam with a color that is suitable to excite the markers. The second radiation beam consists of one or more laser beams with a somewhat different (redder) color that de-excites the marker ("quenching"). The intensity profile of the first radiation beam should have a central maximum, whereas the intensity profile of the second radiation beam should demonstrate a central minimum. De-excitation should preferably occur within a few tens of picoseconds after excitation.

By de-exciting markers in a portion of the excitation region, one can prevent the flux of fluorescence radiation from these markers from being detected, and one can achieve a situation whereby only markers from a portion of the excitation region are detected, which results in a better spatial resolution.

The invention aims to provide a method whereby a better spatial resolution is achieved with the method described in the aforementioned US patent text.

To this end, the method according to the invention is characterized in that:

The second radiation beam is a focused particle beam that is scanned across the sample;

The focus of the particle beam has a cross section smaller than the cross section of the excitation region;

The energy of the particles in the particle beam is sufficient to lower the flux of fluorescence radiation emanating from markers impacted by the particles, as a result of damage;

The position of the focused particle beam with respect to the sample is registered at the instant that the flux decreases by at least a previously determined threshold value.

In response to the excitation, a flux of fluorescence radiation is emitted from the sample. This flux is generated by one or more markers in the sample that are located in the excitation region. If the flux that results from excitation decreases by at least a previously determined threshold value, this has to be because a marker in the excitation region is damaged.

The invention is based upon the insight that, by deliberately causing damage to the marker, the location of the marker can be determined by determining where the particle beam is located at the moment that the decrease in flux occurs as a result of the damage. Such deliberate damage is achieved by firing upon the marker with a focused particle beam.

The generation of a focused particle beam is a technique known per se, and is employed in, for example, Focused Ion Beam (FIB) apparatus, Scanning Electron Microscope (SEM) apparatus, and Environmental Scanning Electron Microscope (ESEM) apparatus. These apparatus can focus a particle beam onto a sample with a cross section of the beam focus of, for example, 1 nm, and can scan this beam across the sample. The energy of the particles in the particle beam in these types of apparatus is generally adjustable from less than 200 eV to more than 20 keV. With these apparatus, it is therefore possible to generate particles with energies that are more than sufficient to damage markers.

It should be noted that the desired damage can not only occur via the interaction of the markers with particles in the focused particle beam, but that the damage can also occur via interaction of the marker with secondary particles, such as X-ray photons and secondary electrons, which are induced by the focused beam in an interaction region. As a result of this, a marker can be damaged even at some distance from the focused particle beam, which can lead to a less accurate determination of position. As is known to the skilled artisan in the field of electron microscopy, the size of the interaction region can be kept sufficiently small via a suitable choice of the particle energy.

In an embodiment of the method according to the invention, the excitation occurs via a photon beam.

By illuminating the sample with photons, the markers will become excited, after which the marker will emit photons in response to this excitation. This illumination can occur using a focused laser beam, but also using a light beam with a broadband spectrum ("white light").

It should be noted that the use of white light is particularly attractive for the purpose of simultaneously detecting several types of markers, seeing as markers can not only differ as regards the type of molecule—such as an antibody—to which they attach themselves, but also as regards the color of light with which they can be excited, and the color of the emitted fluorescence radiation. If several types of marker are present in a sample, the method according to the invention can not only be used to determine the location, but also the type, of marker. This is because, when the detector for detecting the fluorescence radiation is embodied in such a way that, per color—or, in other words, per type of marker—a reduction of the flux of fluorescence radiation of that color (type of marker) can be determined, it is possible to determine not only the location, but also the type, of marker.

In another embodiment of the method according to the invention, the focused particle beam is a focused electron beam.

Electrons are very effective in chemically altering organic materials in particular. In the case of such chemical alteration of, for example, an organic marker, the marker will become so damaged that no more fluorescence radiation will be emitted.

In yet another embodiment of the method according to the invention, the focused particle beam is a beam of ions.

As is known to the skilled artisan, ions with an energy of a few keV have the property of removing the surface of a material on which they impinge (sputtering). This sputtering occurs both for the sample and for the markers located therein. Ions are therefore very effective in causing the desired damage to the markers. An attendant advantage of the use of ions is that a marker that is originally located deep in the sample will slowly emerge at the surface of the sample, after which this marker will be damaged and the position will be determined. In this way, it is possible to make a 3D positional determination of the markers in the sample.

In yet another embodiment of the method according to the invention, a gas is admitted during irradiation with the focused particle beam, so as to make etching possible.

The use of gases in combination with an ion beam or electron beam to remove material from a sample is a technique known per se. This technique is applied, for example, in FIB apparatus. By applying this technique during irradiation of the sample with the focused particle beam, the surface of the sample is etched away during scanning of the particle beam across the sample. In this way, a marker that is originally located deep within the sample will slowly emerge at the surface of the sample, after which this will become damaged and the position will be determined. In this way, it is possible to make a 3D positional determination of the markers in the sample.

Figure 2A:
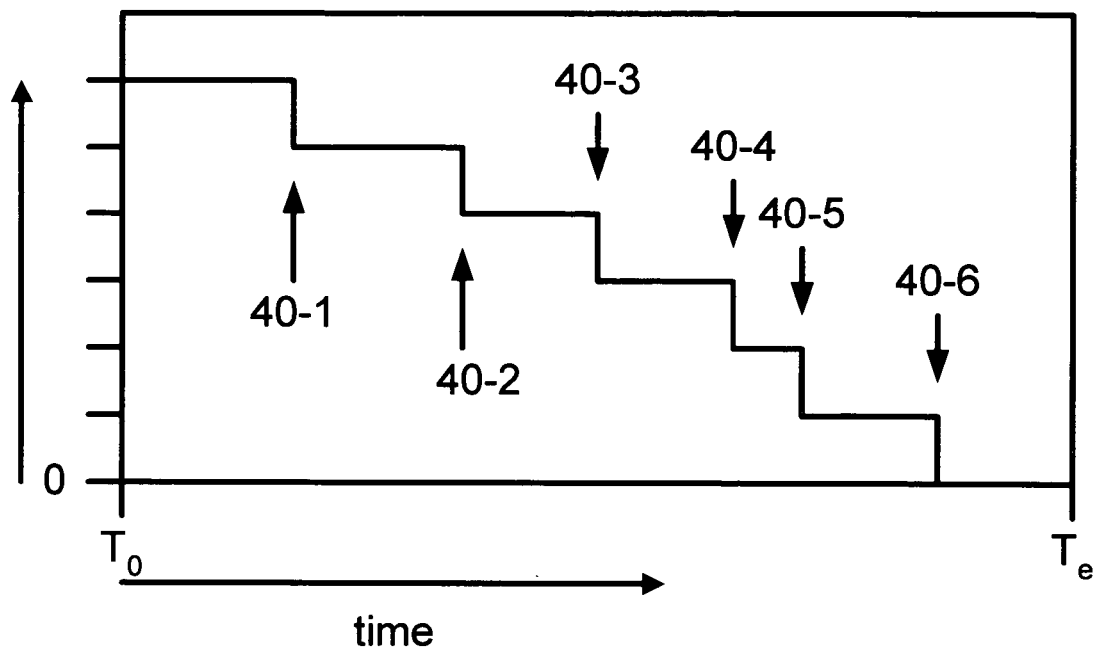
Figure 2B:
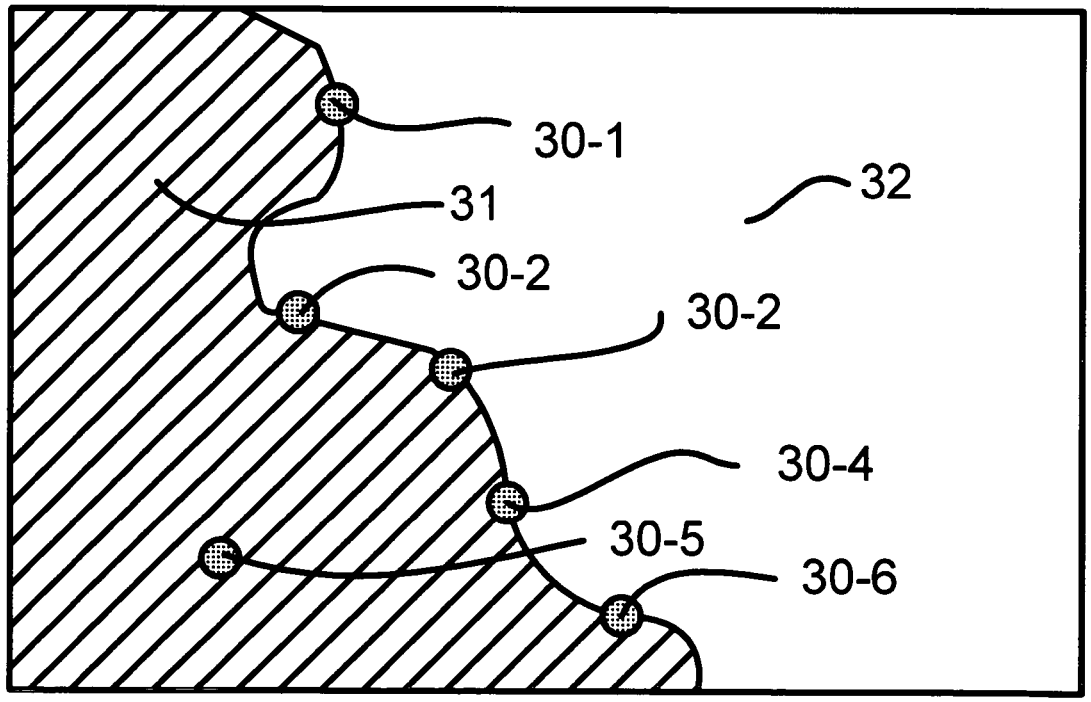

The invention will be further elucidated on the basis of the figures, in which:

FIG. 1 schematically depicts an apparatus for performing the method according to the invention;

FIG. 2A schematically depicts the trend in the flux of fluorescence radiation emanating from the sample during performance of the method, and;

FIG. 2B schematically depicts an image in which there is information originating both from the particle detector and the light detector.

FIG. 1 schematically depicts an apparatus for the performance of the method according to the invention. A particle-optical column 1, such as an ion column, generates a focused particle beam of electrically charged particles 3. The particle beam 3 is focused onto a sample 4 located on a sample holder 5. The focused particle beam 3 is scanned across the sample 4 with the aid of a deflection unit 2.

Charged particles, such as secondary electrons, emanating from the sample are detected by a particle detector 8, such as an Everhardt-Thornley detector.

The vacuum necessary for the focused particle beam 3 is achieved by sealing a vacuum chamber 7 with the aid of sealing means 6 and subsequently evacuating the chamber using (non-depicted) vacuum pumps.

It should be noted that it is advantageous in the case of biological samples to maintain a small residual pressure of water vapor, such that the sample does not dry out. This technique is known per se, and is applied in, for example, ESEMs (Environmental Scanning Electron Microscopes).

Gas injector 9 makes it possible to introduce an etch gas into the vacuum chamber 7, so that material can be removed from the sample 4 under the influence of the focused particle beam 3.

The sample holder 5 is comprised of a transparent material, such as glass. So as to prevent the sample 4 from becoming charged as a result of the irradiation with the focused particle beam 3, a transparent coating of a conductive material can be applied to the glass, for example.

A laser 10 produces a light beam 11 that is focused onto the sample 4 via a semi-transmissive mirror 12 and a lens 13, and via the transmissive sample holder 5. The focused particle beam 3 and the light beam 11 impinge upon the sample at essentially the same position 14. Fluorescence radiation emanating from markers in the sample 4 is detected by detector 16 via the sample holder 5, the lens 13 and the semi-transmissive mirror 12. So as to prevent scattered and reflected light originating from the laser 10 from also being detected, a color filter 15 is placed between the semi-transmissive mirror 12 and light detector 16, which filter does not allow light having the color of the laser to pass, but does allow fluorescence radiation to pass. So as to detect as much light as possible emanating from the sample 4, light that is emitted in a direction away from the detector 16 is reflected by a mirror 17 toward the detector 16.

Control unit 20 sends a control signal to the deflection coils 2 with which the particle beam 3 is scanned across the sample 4. The deflection of the particle beam is hereby generally proportional to the control signal that is supplied to the deflection unit.

The signals emanating from the particle detector 8 at a certain moment emanate from that location on the sample 4 where the particle beam 3 is impinging upon the sample at that moment. By now scanning the particle beam 3 in a raster across the sample 4, and synchronously building up an image 22 on the monitor 21, whereby the brightness is proportional to the signal from the particle detector 8, an image 22 of the scanned region of the sample 4 becomes visible on monitor 21. This image build-up is also done by the control unit 20.

In addition, the control unit 20 controls the laser 10, and thereby turns the light beam on and off.

The control unit 20 also receives the signal from the light detector 16, and determines on the basis of that signal whether a significant reduction of the flux of fluorescence radiation is occurring. "Significant" should hereby be understood as referring to a reduction by at least a previously determined threshold value. At the moment that such a significant reduction occurs, the position of the particle beam 3 is known, because this position is controlled via the driving of the scanning coils 2. The control unit 20 can now cause an indication, such as a bright spot or a spot of a different color, to appear at the corresponding position on the screen 21.

If markers are present in the region across which the beam is scanned, these will be impacted upon by the particle beam during scanning. As a result hereof, damage to the marker will occur.

FIG. 2A schematically depicts the flux of fluorescence radiation emanating from the sample. At the start of scanning, at instant $T=T_o$, a number of markers will fluoresce—in this case, 6 markers. During scanning, these markers will each be damaged. As a result of such damage, the flux will decrease. This is schematically indicated in FIG. 2A at instant 40-$i$, whereby $i$ is the $i_{th}$ marker to be damaged. By depicting in image 22—which depicts the signal emanating from the particle detector 8—a bright point or a point that is different in color at the moment that such a change in flux occurs, it will be easily visible where the marker is located on the sample.

It should be noted that, using current computer techniques, it is also possible to apply in the image 22 a symbol of another form—such as crosses, rectangles, etc.—that indicates the location of the fluorescent marker.

FIG. 2B schematically depicts an image in which there is information originating both from the particle detector 8 and the light detector 16.

The particle detector 8 (an Everhardt-Thornley detector) makes it possible to generate an image 22 in which regions with different yields of secondary particles are imaged using different brightnesses (31, 32). In this image 22, it is also indicated at which positions 30-$i$ of the particle beam a significant reduction of the flux was determined, or, in other words, where a marker is located. In this manner, it is possible to see in an easy manner where the markers are located on the sample.

It should be noted that embodiments are possible whereby the light detector 16 is capable of distinguishing, and separately processing light from, different markers, characterized by different fluorescence colors.

In this way, it is possible to simultaneously detect different types of markers—and to use differently colored bright points or symbols, for example, in the image 22—so as to be able to distinguish the different types of markers.

It should also be noted that, should a marker cease emitting photons for a reason other than as a result of being damaged by the charged particle beam 3, this will lead to depiction of that marker at an incorrect location. This is because the light detector 16 will detect that the quantity of fluorescence radiation is decreasing, and the control unit 20 will depict the marker on image 22 at the location corresponding to the particle beam 3 at that moment, even if the beam position has no relation to the presence of a marker at that position.

It is therefore highly undesirable that a marker should stop fluorescing for any reason other than as a result of being fired at by the particle beam 3.

The lifetime of some markers, particularly some organic markers, is limited to $10^5$ emitted photons, for example. It is therefore desirable to scan the entire excitation region within the timeframe in which a marker emits $10^5$ photons.

It should be noted that it is of importance to center the excitation region and the scan region w.r.t. one another. When these two regions are centered on one another, they will generally not rapidly become de-centered. Such centering can therefore be performed as a periodic adjustment. One can think of various ways in which such centering can be determined.

One possible adjustment comprises imaging a hole in a slidable diaphragm plate with the aid of the particle beam and the particle detector, whereby the hole has a diameter that is approximately equal to the diameter of the focus of the laser beam. The diaphragm plate can now be slid until it is centered w.r.t. the region scanned by the particle beam. By subsequently directing the laser onto the diaphragm plate, and aiming it in such a way that a maximum quantity of light is admitted through the hole, both regions will be centered on one another. Detection of the quantity of admitted light can occur with the aid of, for example, a non-depicted light detector in the vacuum chamber.

It should be noted that the illumination of the sample 4 by the laser beam 11 can be a continuous illumination, but that it can also consist of a series of pulses.

It should also be noted that, although in the depicted embodiment of an apparatus for performing the method, the particle beam 3 and the light beam 11 impinge upon the sample 4 from opposed directions, it is also possible to embody the apparatus in such a manner that the beams (3, 11) impinge upon the sample 4 from virtually the same direction. This is particularly advantages for relatively thick samples, whereby the exciting laser beam cannot penetrate through the entire sample.

The invention claimed is:

1. A method of determining the location of markers that are excitable by radiation in a sample to be investigated, comprising:

providing a sample having markers;

irradiating the sample with a first radiation beam, as a result of which an excitation region is formed in the sample, in which excitation region markers are excited;

detecting fluorescence radiation emanating from markers in response to the excitation, and;

reducing, with the aid of a second radiation beam, the detectable fluorescence radiation in a portion of the excitation region, characterized in that:

the second radiation beam is a focused particle beam that is scanned across a portion of the sample, the portion including at least a portion of the excitation region;

the focus of the particle beam has a cross section smaller than the cross section of the excitation region;

the energy of the particles in the particle beam is sufficient to lower the flux of fluorescence radiation emanating from markers impacted by the particles; and the position of the focused particle beam with respect to the sample at the time that the flux decreases by at least a previously determined threshold value is registered.

2. A method according to claim 1, wherein the cross section of the particle beam is at least ten times smaller than the cross section of the excitation region.

3. A method according to claim 1, wherein excitation occurs with a photon beam.

4. A method according to claim 1, wherein the focused particle beam is a focused electron beam.

5. A method according to claims 1, wherein the focused particle beam is a focused ion beam.

6. A method according to claim 1, wherein a gas is admitted during irradiation with the focused particle beam, so as to etch.

7. A device embodied to perform the method according to claim 1, comprising:

means for generating a first radiation beam to excite a marker;

detection means for detecting a flux of fluorescence radiation emanating from excited markers;

means for generating a second radiation beam, characterized in that:

the means for generating the second radiation beam generate a focused particle beam, which particle beam is scanned across the sample, and;

registration means are present to determine the position of the focused particle beam with respect to the sample in dependence upon a previously determined reduction in the detected flux.

8. The method according to claim 2, wherein excitation occurs with a photon beam.

9. A method according to claim 2, wherein the focused particle beam is a focused electron beam or a focused ion beam.

10. A method according to claim 3, wherein the focused particle beam is a focused electron beam or a focused ion beam.

11. An apparatus for determining the location of markers that are excitable by radiation in a sample to be investigated, comprising:

a radiation source adapted to excite markers;

a detector for detecting radiation emanating from excited markers;

a charged particle beam source for generating a focused particle beam and directing the focused particle beam toward the sample in the vicinity of a marker; and a controller programmed to determine the position of the focused particle beam with respect to the sample when the detector detects a reduction exceeding a predetermined threshold in the radiation emanating from the markers.

12. The apparatus of claim 11 in which the charged particle beam source is an electron source.

13. The apparatus of claim 11 in which the charged particle beam source is an ion source.

14. The apparatus of claim 11 in which the detector can separately detect different colors to detect fluorescence radiation from different types of markers.

15. A method of determining the location in a sample of markers that are excitable by radiation, comprising:

providing a sample having fluorescent markers;

irradiating the sample with a first radiation beam to excite markers in an excitation region in the sample;

detecting radiation emanating from markers in response to the excitation;

directing a charged particle beam toward at least a portion of the excitation region; and determining the position of the charged particle beam when the radiation from markers in the excitation region decreases by at least a previously determined threshold value, the position of the charged particle beam at that time indicating the position of a marker.

16. The method of according to claim 15, wherein the charged particle beam has a cross section smaller than the diameter of the excitation region.

17. The method of according to claim 16, wherein the cross section of the charged particle beam is at least ten times smaller than the cross section of the excitation region.

18. The method of according to claim 15, wherein the charged particle beam is an electron beam or an ion beam.

19. The method of according to claim 15, wherein directing a charged particle beam toward at least a portion of the excitation region includes scanning the charged particle beam over an area including at least a portion of the excitation region.

20. The method of according to claim 15, wherein detecting radiation emanating from markers includes detecting radiation of different colors and in which determining the position of the charged particle beam when the radiation from markers in the excitation region decreases by at least a previously determined threshold value includes separately determining the position of the charged particle beam when the radiation of different colors decreases by at least previously determined threshold values.

* * * * *

UNITED STATES PATENT AND TRADEMARK OFFICE
CERTIFICATE OF CORRECTION

PATENT NO. : 7,317,515 B2  Page 1 of 1
APPLICATION NO. : 11/268975
DATED : January 8, 2008
INVENTOR(S) : Bart Buijsse and Robert Frans Maria Hendricks It is certified that error appears in the above-identified patent and that said Letters Patent is hereby corrected as shown below:

Page 1, Column 1:
(73) Please add Assignee information to read: -- Assignee: FEI Company, Hillsboro, OR (US) and Koninklijke Philips Electronics N.V., Eindhoven (NL) --.

Column 4, Line 15:
Please change "per se" to read -- *per se* --.

Column 4, Line 52:
Please change "per se" to read -- *per se* --.

Column 5, Line 51:
Please change "$i_{th}$" to read -- $i^{th}$ --.

Signed and Sealed this

Fifth Day of August, 2008

JON W. DUDAS
*Director of the United States Patent and Trademark Office*